United States Patent
Donabauer et al.

(10) Patent No.: US 10,207,248 B2
(45) Date of Patent: Feb. 19, 2019

(54) METHYL IODIDE ADSORBER, USE THEREOF AND METHOD FOR THE ADSORPTION OF METHYL IODIDE

(71) Applicant: Clariant Produkte (Deutschland) GmbH, Frankfurt am Main (DE)

(72) Inventors: Katharina Donabauer, Bruckmuehl (DE); Arno Tissler, Tegernheim (DE); Mika Endler, Rosenheim (DE); Olaf Buttner, Kolbermoor (DE)

(73) Assignee: Areva GmbH, Erlangen (DE)

( * ) Notice: Subject to any disclaimer, the term of this patent is extended or adjusted under 35 U.S.C. 154(b) by 74 days.

(21) Appl. No.: 14/358,975

(22) PCT Filed: Apr. 2, 2013

(86) PCT No.: PCT/EP2013/056941
§ 371 (c)(1),
(2) Date: May 16, 2014

(87) PCT Pub. No.: WO2013/150029
PCT Pub. Date: Oct. 10, 2013

(65) Prior Publication Data
US 2015/0110697 A1  Apr. 23, 2015

(30) Foreign Application Priority Data

Apr. 2, 2012 (DE) .................. 10 2012 006 542

(51) Int. Cl.
| | | |
|---|---|---|
| *B01D 53/02* | (2006.01) | |
| *B01J 20/18* | (2006.01) | |
| *B01J 20/04* | (2006.01) | |
| *B01J 20/28* | (2006.01) | |
| *G21F 9/02* | (2006.01) | |
| *B01J 20/02* | (2006.01) | |

(52) U.S. Cl.
CPC .............. *B01J 20/18* (2013.01); *B01D 53/02* (2013.01); *B01J 20/0207* (2013.01); *B01J 20/0233* (2013.01); *B01J 20/0251* (2013.01); *B01J 20/0255* (2013.01); *B01J 20/04* (2013.01); *B01J 20/186* (2013.01); *B01J 20/28064* (2013.01); *B01J 20/28069* (2013.01); *G21F 9/02* (2013.01); *B01D 2253/1085* (2013.01); *B01D 2253/1122* (2013.01); *B01D 2253/306* (2013.01); *B01D 2253/31* (2013.01); *B01D 2257/202* (2013.01); *B01D 2257/2068* (2013.01)

(58) Field of Classification Search
None
See application file for complete search history.

(56) References Cited

U.S. PATENT DOCUMENTS

| | | | |
|---|---|---|---|
| 3,852,407 A * | 12/1974 | Schmitt .................... | G21F 9/06 423/101 |
| 4,735,786 A | 4/1988 | Inoue et al. | |
| 4,913,850 A | 4/1990 | Puppe et al. | |
| 5,075,084 A | 12/1991 | Wilhelm et al. | |
| 5,962,735 A | 10/1999 | Kulprathipanja | |
| 6,380,428 B1 | 4/2002 | Kulprathipanja | |
| 2001/0031299 A1 | 10/2001 | Full et al. | |
| 2008/0282884 A1* | 11/2008 | Kelley .................. | B01D 53/02 95/96 |
| 2012/0051488 A1 | 3/2012 | Eckardt et al. | |

FOREIGN PATENT DOCUMENTS

| | | |
|---|---|---|
| CN | 1277885 | 12/2000 |
| CN | 101829542 A | 8/2010 |
| CN | 101811023 A | 9/2010 |
| DE | 296899 A5 | 12/1991 |
| EP | 0 175 435 A1 | 3/1986 |
| EP | 0 379 895 A1 | 8/1990 |
| EP | 2 423 923 A2 | 2/2012 |
| JP | S58-91032 | 5/1983 |
| JP | S60-225638 | 11/1985 |
| JP | S61-68127 | 4/1986 |

OTHER PUBLICATIONS

Chinese Office Action dated Feb. 15, 2015 for Chinese Application No. 20138003133.8.
Korean Office Action for corresponding Korean Application dated Jun. 17, 2015.
Japanese Office Action for Application No. 2014-542900 dated Oct. 17, 2014.
Stelzer et al., "Hydophobic properties of all-silica zeolite beta", Microporous and Mesoporous Materials vol. 22, 1998, pp. 1-8.
Jubin, "A Literature Survey of Methods to Remove Iodine from Off-Gas Streams Using Solid Sorbents", Oak Ridge National Laboratory, Apr. 1979.
International Search Report dated Jun. 28, 2013 for corresponding International Application No. PCT/EP2013/056941.
Coombs, D.S., et al., "Recommended Nomenclature for Zeolite Minerals: Report of the Subcimmittee on Zeolites of the International Mineralogical Association, Commission on New Minerals and Mineral Names," The Canadian Mineralogist, vol. 35, 1997, pp. 1571-1606.
Brunauer et al., "Adsorption of Gases in Multimolecular Layers," J. Am. Chem. Soc., vol. 60, pp. 309-319 (1938).
Office Action dated Nov. 9, 2012 in counterpart application DE 10 2012 006 542.6, including English translation.
India Examination Report for India Application No. 8574/DELNP/2014 dated Feb. 20, 2018.

* cited by examiner

*Primary Examiner* — Anita Nassiri-Motlagh
(74) *Attorney, Agent, or Firm* — RatnerPrestia

(57) ABSTRACT

A methyl iodide adsorber, comprising a zeolite containing at least one iodide-adsorbing metal or a compound thereof, wherein the zeolite is a hydrophobic zeolite. Also, a use of the adsorber and a method for the adsorption of methyl iodide.

34 Claims, No Drawings

METHYL IODIDE ADSORBER, USE THEREOF AND METHOD FOR THE ADSORPTION OF METHYL IODIDE

CROSS-REFERENCE TO RELATED APPLICATIONS

This application is a U.S. National Phase application of PCT International Application No. PCT/EP2013/056941, filed Apr. 2, 2013, and claims priority to German application DE 10 2012 006 542.6, filed Apr. 2, 2012, the entire contents of each being incorporated herein by reference in their entirety.

FIELD OF INVENTION

The present invention relates to a methyl iodide adsorber, a use thereof and a method for the adsorption of methyl iodide.

BACKGROUND

In nuclear power plants all components that come into contact with radioactive substances are contained in the so-called "nuclear island". This comprises the safety container (inner containment) with primary circuit, the flood basin and the core catcher. In the top part of the safety container catalytic recombiners or recombiner systems can be installed, for example with Pd on $Al_2O_3$, which are meant to limit the proportion of hydrogen in the atmosphere, in order to prevent hydrogen explosions.

In fission reactors, during normal operation, but in particular in the event of a failure, in addition to the solid decay isotopes of uranium, or daughter isotopes arising from the uranium fission and higher isotopes resulting from neutron capture, gaseous radioactive compounds also occur, which must on no account be released into the environment. The most important of these, in addition to hydrogen, are radioactive iodine and methyl iodide.

Hydrogen is produced in small quantities in normal operation and in large quantities in the event of failures which are associated with a significant increase in temperature due to the reaction of water with the metal casing of the fuel rods. This hydrogen can then, in a detonating gas explosion, lead to the destruction of the safety container and to the release of large quantities of radioactive material (e.g. the accidents at Chernobyl and Fukushima). In order to avoid such disasters, more recently nuclear power plants are being equipped or retrofitted with recombiner systems. These are passive systems, the object of which is to catalytically reoxidize hydrogen formed at room temperature under atmospheric conditions, to form water vapour and thus avoid the production of explosive atmospheres. Recombiners can also be used for spent fuel pools and fuel element containers, ensuring that the hydrogen released can react to form water before it reaches an explosive concentration.

From the fission products caesium and iodine, caesium iodide is also produced in the fuel rods, which, unless it is retained in the fuel rods, collects in the reactor sump. Due to radiolysis or at hot spots (e.g. at hot spots in hydrogen recombiners) elemental iodine is formed from caesium iodide in the reactor sump, and can escape from the reactor sump due to its volatility, even in normal operation. Due to its reactivity with organic substances from the reactor environment (e.g. dye), free iodine can then react to form methyl iodide. These volatile radioactive substances accumulate in the gas stock inside the reactor shell and have to be adsorbed from there. Many of the compounds formed are also present aerosol-bound and are released in the event of a failure.

A majority of the radioactive iodine isotopes formed have a short half-life and thus, due to the high radiological activity in the event of a failure, contribute very significantly to the danger to life. Iodine is taken up in the thyroid gland and, at high concentrations, causes thyroid cancer. In particular iodine 131 with a half-life of 8 days may be mentioned here.

There is therefore a need for radioactive methyl iodide adsorbers that are stable even under high humidity, for equipping nuclear reactors or for retrofitting in safe operation or to ensure the safety of the reactor when shut down or during or after decommissioning.

Based on new knowledge and safety conditions, the retention of organic methyl iodide has now become a challenge, which is also a lesson learnt from the Fukushima incident of 2011. Until now there has been no technical solution. However, various approaches have been pursued. Adsorbent materials for the deposition of elemental iodine are known, such as e.g. aluminium oxides loaded with silver. However, due to inhibition, these are not very useful under water vapour.

Until now there has been no operational technically sophisticated measure for depositing methyl iodide. It is known that silver-containing adsorbent materials are suitable for the adsorption of methyl iodide. The silver iodide formed has a melting point of ca. 600° C. and a boiling point of ca. 1500° C., and is therefore largely stable under normal conditions. However, in the case of known adsorbent materials, under high water vapour concentrations, it is possible for water to be incorporated in the porous structures of the adsorber and thus inhibit the adsorption of methyl iodide. A possibility for preventing this inhibition is silanization of the outer adsorber surface by means of organic silane compounds. This method is expensive and presents serious technical problems. The silane layer decomposes as from ca. 180° C., generating considerable heat. This means that, starting from this temperature no further adsorption of methyl iodide can take place and furthermore, any hydrogen that may be present will possibly be ignited due to the highly exothermic conditions, which may lead to the undesired concomitant phenomenon of an explosion.

SUMMARY

The object was therefore to provide an absorbent material with which the abovementioned disadvantages are avoided and which is, in addition, characterized by a high stability and a high iodide adsorption capacity.

This object was achieved by a methyl iodide adsorber comprising a zeolite containing at least one iodide-adsorbing metal or a compound thereof, wherein the zeolite is a hydrophobic zeolite, a use thereof for the adsorption of methyl iodide, radioactive methyl iodide, iodine and/or radioactive iodine, and a method for the adsorption of methyl iodide, in which methyl iodide is brought into contact with the adsorber.

In an embodiment a methyl iodide adsorber is specified, comprising a zeolite containing at least one iodide-adsorbing metal or a compound thereof, wherein the zeolite is a hydrophobic zeolite.

Another embodiment relates to the use of a methyl iodide adsorber comprising a zeolite containing at least one iodide-adsorbing metal or a compound thereof, wherein the zeolite is a hydrophobic zeolite, for the adsorption of methyl iodide, radioactive methyl iodide, iodine and/or radioactive iodine.

According to a further embodiment, in a method for the adsorption of methyl iodide, methyl iodide is brought into contact with an adsorber comprising a zeolite containing at least one iodide-adsorbing metal or a compound thereof, wherein the zeolite is a hydrophobic zeolite.

Surprisingly the adsorber of the embodiments is highly hydrophobic, exhibits a high iodide adsorption capacity and is stable in terms of these properties over a wide range of water vapour concentration and temperature. Furthermore, the risk of an exothermic ignition of any hydrogen that may be present is clearly reduced due to the hydrophobic properties and the absence of a silane layer possibly desorbing under exothermic conditions.

Further features and functionalities can be found in the following description of embodiments, the figures and the dependent claims.

All the features of embodiments which are described here and are not mutually exclusive can be combined with each other. Elements of one embodiment can be used in the other embodiments without further mention. Embodiments of the invention are now described in more detail by means of the following examples, without wishing thereby to limit these.

DETAILED DESCRIPTION

In the following description of embodiments the methyl iodide adsorber is also simply called adsorber. In addition in the following description the terms zeolite and zeolite material are used synonymously. The term "metal or a compound thereof" can be understood as a precursor of the metal or a compound of a precursor of the metal or comprise such a precursor. In addition the metal can be present in ionic form. Furthermore the term "promoter" can be understood as a precursor of the promoter, as a compound of the promoter or as a compound of a precursor of the promoter or comprise such a precursor.

The expression "iodide-adsorbing metal" comprises or represents a metal that adsorbs iodide and in embodiments also iodine physically and/or chemically. For example, if silver is used as the iodide-adsorbing metal in embodiments, it reacts with methyl iodide, forming silver iodide and thus binds the methyl iodide in the adsorber by chemical adsorption.

Furthermore, the embodiments of the invention are described below with reference to a silver-containing hydrophobic zeolite, without the invention being limited to this noble metal.

The term "comprising" includes in embodiments "substantially consisting of" or "consisting of" and can be replaced by these terms. This accordingly applies to grammatical variations of the word "comprising". Furthermore, for the description of value ranges, it is true here that the specification of a broad range with narrower alternatives or preferred ranges also discloses ranges which can be formed by any combination of specified lower range limits with specified upper range limits.

In an embodiment a methyl iodide adsorber is specified, comprising a zeolite containing at least one iodide-adsorbing metal or a compound thereof, wherein the zeolite is a hydrophobic zeolite. The iodide-adsorbing metal is a metal also absorbing iodine in embodiments. The adsorber can also adsorb elemental iodine, e.g. with adsorption rates greater than 99%.

The iodide-adsorbing metal can for example be selected from silver (Ag), yttrium, cerium, magnesium, sodium, tin and lead. In embodiments it is also possible for several of these iodide-adsorbing metals to be used. Furthermore, one or more of the iodide-adsorbing metals can be contained in its cationic form. Silver is preferably used as the iodide-adsorbing metal. When silver is used as the iodide-adsorbing metal the vapour pressure of the silver iodide produced, with a boiling point of 1500° C., is very low and the radioactive iodide is thus securely bound in the adsorber.

If during nuclear meltdown a temperature above ca. 1200° C. is reached, the radioactive iodide is not released from the adsorber of embodiments but is vitrified in the true sense of the word, due to the transformation of the zeolite into a thermodynamically more stable structure (cristobalite or quartz), and is thus up to melting securely stored in the quartz or in the cristobalite, respectively, up to temperatures of ca. 1700° C.

As explained above, the methyl iodide adsorber of embodiments is hydrophobic and in addition, surprisingly exhibits a pronounced iodide adsorption ability. In embodiments this can lead to an iodide deposition greater than 99%. Furthermore, the methyl iodide adsorber is stable in terms of these properties over a wide range of water vapour concentration and temperature. In particular the hydrophobicity, i.e. the degree of water-repellency, is stable even at high temperatures. Furthermore, the risk of an exothermic ignition of any hydrogen that may be present is clearly reduced by the hydrophobic properties. These effects are for example to be observed when, if the zeolite used in the production, which is not loaded with an iodide-adsorbing metal or is undoped, is hydrophobic per se, i.e. if it has a high "intrinsic" hydrophobicity. In some examples the hydrophobicity of the zeolite and/or of the adsorber can in addition also be retained at high temperatures up to the destruction of the zeolite structure above 1000° C.

Furthermore, because of the hydrophobic properties of the zeolite used in embodiments, no coating, e.g. with organo-silicon compounds, or other measures are required to make the zeolite loaded with the iodide-adsorbing metal or the adsorber hydrophobic. As a result, regeneration of the adsorber is made possible by heating. The hydrophobic properties of the zeolite are not adversely affected by high temperatures in embodiments of the invention. Moreover, the quantity of the decomposition products produced is clearly reduced in comparison with adsorbers which have hydrophobic coatings.

In the context of the present invention, by a zeolite or zeolite material, according to a definition of the International Mineralogical Association (D. S. Coombs et al., Can. Mineralogist, 35, 1997, 1571) is meant a crystalline substance with a structure characterized by a framework of interconnected tetrahedra. Each tetrahedron consists of four oxygen atoms surrounding one central atom, wherein the framework contains open cavities in the form of channels and cages which are normally occupied by water molecules and extra-framework cations which can be exchanged. The channels of the material are large enough to allow access to guest compounds. In the case of hydrated materials, dehydration usually takes place at temperatures below approximately 400° C. and is for the most part reversible.

The zeolite material that can be used in embodiments can be for example a silicate, an aluminium silicate, a silicon aluminium phosphate, a metal aluminium phosphosilicate, a gallium aluminium silicate, a boroaluminium silicate, or a titanium silicoaluminophosphate (TAPSO), wherein aluminium silicates, also referred to as aluminium silicate zeolites are particularly preferred. The zeolite used in embodiments can, furthermore, be characterized by a high proportion of $SiO_2$, which for example exceeds 85 wt. %, preferably 98 wt. %.

By the term "aluminium silicate" according to the definition of the International Mineralogical Association (D. S. Coombs et al., Can. Mineralogist, 35, 1997, 1571) is meant a crystalline substance with a three-dimensional network structure of general formula $M^{n+}[(AlO_2)_x(SiO_2)_y] \cdot xH_2O$ which is made up of $SiO_{4/2}$ and $AlO_{4/2}$ tetrahedra that are connected by common oxygen atoms to form a regular three-dimensional network. The Si/Al atomic ratio=y/x is always greater than/equal to 1 in accordance with the so-called "Löwenstein's rule", whereby two adjacent negatively charged $AlO_{4/2}$ tetrahedra cannot occur adjacently. The $SiO_2/Al_2O_3$ ratio in an aluminium silicate zeolite is also referred to as a modulus.

In a further embodiment of the adsorber the zeolite is an intrinsically hydrophobic zeolite, i.e. the zeolite not loaded with the iodide-adsorbing metal is already hydrophobic. This has the surprising result that the zeolite containing the iodide-adsorbing metal and thus also the adsorber of embodiments are also hydrophobic without further excipients or measures. Within the context of the invention it has namely been shown that doping with the iodide-adsorbing metal changes the hydrophobicity/hydrophilicity of a zeolite only slightly. Due to the intrinsic hydrophobicity, further treatment of the zeolite used, in order to produce or enhance its hydrophobic properties, becomes superfluous. Furthermore, due to the intrinsic hydrophobicity the fresh adsorber, as well as adsorber stored for a longer period or used adsorber, is ready for use without further regeneration such as e.g. drying.

In further embodiments of the adsorber the zeolite is an aluminium silicate and/or has an $SiO_2$ proportion >94 wt. %, preferably >98 wt. %. Embodiments in which aluminium silicate zeolites with an $SiO_2$ proportion >94 wt. %, preferably >98 wt. % are used are preferred. The approximate $SiO_2$ proportions as a function of the $SiO_2/Al_2O_3$ modulus are:

| $SiO_2/Al_2O_3$ | wt. % $SiO_2$ |
| --- | --- |
| 10 | 85 |
| 20 | 92 |
| 30 | 94 |
| 50 | 97 |
| 100 | 98 |
| 150 | 99 |

In embodiments of the invention the zeolite used, even in the state not loaded with the iodide-adsorbing metal, has an $SiO_2/Al_2O_3$ ratio >5, preferably >20, further preferably >30, even more preferably >50, in particular >100. It has surprisingly been found that only such a high $SiO_2/Al_2O_3$ ratio brings about sufficiently hydrophobic properties of the zeolite not loaded with the iodide-adsorbing metal and/or loaded with the iodide-adsorbing metal, as well as of the entire adsorber. According to some embodiments the $SiO_2/Al_2O_3$ ratio of the zeolite used lies in the range >100 or >140, e.g. between 100 and 250 or between 130 and 170.

The zeolite material used in embodiments can preferably correspond to one of the following structure types: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EON, EPI, ERI, ESV, ETR, EUO, EZT, FAR, FAU, FER, FRA, GIS, GIU, GME, GON, GOO, HEU, IFR, IHW, ISV, ITE, ITH, ITW, IWR, IWV, IWW, JBW, KFI, LAU, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, VET, VFI, VNI, VSV, WEI, WEN, YUG and ZON, wherein zeolite materials preferably have a 12-ring pore system (BEA, FAU) and are particularly preferably of Beta structure type (BEA). The above three letter code nomenclature corresponds to the "IUPAC Commission of Zeolite Nomenclature". In addition, according to embodiments of the invention, the zeolite can be selected from the group consisting of AFI, AEL, BEA, CHA, EUO, FAU, FER, KFI, LTL, MAZ, MOR, MEL, MTW, OFF, TON and MFI. The named zeolite structure types are suitable for the purposes of the invention as, with them, the desired hydrophobic properties and/or the desired activity can be realized particularly advantageously with a low metal load of the adsorber.

According to further embodiments the zeolite can be microporous. Furthermore, the zeolite or adsorber, in particular in the case of an adsorber which contains the zeolite and is formed as shaped bodies or in the case of a washcoat which contains the zeolite and is arranged on a support, can have a proportion of micropores of more than 70%, preferably more than 80%, relative to the total pore volume of the zeolite or adsorber. In the context of the present invention, by the terms micropores, mesopores and macropores is meant pores which have a diameter of <1 nanometer (micropores), a diameter of from 1 to 50 nanometers (mesopores), or a diameter of >50 nanometers (macropores) respectively.

The microporosity of the zeolite according to embodiments brings about a strong and stable dispersity of the iodide-adsorbing metal in the zeolite because, due to the microporous and uniform pore structure of the zeolite, the metal is strongly forced into the dispersion and is thus evenly distributed throughout the zeolite. In addition, this promotes the absorption of iodide into the zeolite because, in comparison with similarly loaded other structures, such as e.g. aluminium oxide, the zeolite of embodiments exhibits an increased iodide adsorption capacity. In addition, in embodiments, the vapour pressure of the metal which has adsorbed iodide is reduced due to the microporous structure. For example, when silver is used as the iodide-adsorbing metal, the vapour pressure of the silver iodide produced is very low, with a boiling point of 1500° C. In addition, if a temperature above ca. 1200° C. is reached, in the case of nuclear meltdown, the radioactive iodide is not released, but, due to the transformation of the zeolite into a thermodynamically more stable structure (cristobalite or quartz), vitrified in the true sense of the word, and is thus up to melting securely stored in the quartz or in the cristobalite, respectively, up to temperatures of ca. 1700° C.

In a preferred embodiment of the adsorber the iodide-adsorbing metal can substantially be situated in the pores of the zeolite. This also leads to a strong and stable dispersity of the metal in the zeolite, because the metal is thus additionally strongly forced into the dispersion and is thus evenly distributed throughout the zeolite. In addition, this promotes the absorption of iodide in the zeolite. Furthermore, an agglomeration of the iodide-adsorbing metal to form larger particles at high temperatures, which would lead to a loss of effective surface area and thus of performance, is thereby clearly slowed down or prevented.

The iodide-adsorbing metal, e.g. silver, can for example be introduced into the zeolite by ion exchange or by impregnation. The iodide-adsorbing metal can be present in the zeolite in the form of particles. Furthermore, the particles can have an average diameter of from 0.5 to 5 nm, preferably 0.5-1.5 nm and are thus preferably XRD amorphous.

The adsorber of embodiments can contain at least one promoter for reducing the water decomposition by the iodide-adsorbing metal. As the iodide-adsorbing metal can be for example a noble metal, a catalytic decomposition of the water to form hydrogen and oxygen can occur at increased temperatures and water vapour concentrations. This problem is solved according to embodiments due to the doping of the methyl iodide adsorber with the promoter.

The promoter can for example comprise lead (Pb). The iodide adsorption capacity is not reduced by the promoter, rather the water-decomposition tendency of the iodide-adsorbing metal is reduced and thus the formation of hydrogen gas is avoided.

In further embodiments the content of iodide-adsorbing metal in the zeolite or in the adsorber is 0.1 to 50 wt. %, more preferably 5 to 30 wt. %, and most preferably 10 to 20 wt. %. Furthermore, the content of promoter or lead in the zeolite or in the adsorber can be 1 to 30 wt. %, more preferably 5 to 30 wt. %, further preferably 10 to 20 wt. %, and most preferably 3 to 6 wt. %.

The BET surface area of the zeolite or of the adsorber of embodiment examples can be 10 to 1000 $m^2/g$, preferably 300 to 900 $m^2/g$, particularly preferably 500 to 700 $m^2/g$ and/or the integral pore volume of the zeolite or of the adsorber of embodiment examples can be greater than 100 $mm^3/g$, preferably greater than 200 $mm^3/g$. The adsorption capacity of the adsorber can be favourably influenced by these properties individually or in combination.

The adsorber of embodiment examples can be formed as bulk material. The adsorber can furthermore be formed for example as extrudate, as shaped bodies or as particles coated with the zeolite. For example the bulk material can consist of shaped bodies or pellets which have been produced by pressing or extrusion of a ceramic mass of the zeolite loaded with iodide-adsorbing metal.

Spheres, rings, cylinders, hollow cylinders, trilobes or cones, may be mentioned as examples of geometric shapes of the adsorber or shaped bodies wherein a monolith, for example a monolithic honeycomb body, is particularly preferred.

Furthermore, the adsorber can comprise a support to which the zeolite or a washcoat containing the zeolite is applied. A suspension or a slurry of the zeolite in a suspending agent, e.g. in water, optionally with the addition of a preferably silicate binder, serves as washcoat. The zeolite can be applied to the support for example by coating with a suspension or with the washcoat or by growing from a solution.

The adsorber and/or the support can be honeycomb-shaped or plate-shaped, e.g. formed as sheets. The plate-shaped variant allows a parallel installation of several adsorbers in the upper region of the safety container of nuclear power plants, whereby it is possible to achieve a good flow through the adsorbers with the gas containing the methyl iodide.

In addition, in connection with a washcoat it is preferable if the adsorber, to the extent that it is honeycomb-shaped, contains an iodide-adsorbing metal load of from 0.1 to 4.0 g/l, more preferably 0.4 to 1.5 g/l, and most preferably 0.4 to 1.0 g/l, relative to the volume of the honeycomb body.

In embodiments, the support can comprise a metal oxide as support material, preferably a titanium oxide, a cerium oxide, an aluminium oxide, a tin oxide, a zirconium oxide, a silicon oxide, a zinc oxide, an aluminium oxide-silicon oxide or a magnesium silicate or a mixture of two or more of the above-named oxides. Supports or support bodies made of ceramic material can be used. The ceramic material is frequently an inert material with a low surface area such as cordierite, mullite, alpha-aluminium oxide, silicon carbide or aluminium titanate. However, the support material used can also consist of material with a high surface area such as gamma-aluminium oxide or $TiO_2$. Metals can also be used as support material. Preferred supports or support bodies are therefore also formed for example from a sheet, made of any metal or a metal alloy, having a metal foil or sintered metal foil or a metal fabric and produced for example by extrusion, winding, or stacking.

Furthermore, the adsorber of embodiments can be used for the adsorption of methyl iodide, radioactive methyl iodide, iodine and/or radioactive iodine. The adsorber can in particular be used in or in the vicinity of nuclear power plants, reprocessing plants or fuel element storage facilities, e.g. in safety containers or spent fuel pools of nuclear power plants or in containers for irradiated or spent fuel elements.

Moreover, the adsorber can be used together with a hydrogen recombination catalyst, also referred to as a recombinator. This can be used instead of or in addition to a promoter contained in the adsorber. In this way it is possible to avoid or prevent decomposition of the water to hydrogen and oxygen catalyzed by the iodide-adsorbing metal at increased temperatures and/or at increased water vapour concentrations.

A further embodiment relates to a method for the adsorption of methyl iodide, in which methyl iodide is brought into contact with an adsorber according to the abovementioned embodiments. In addition to the methyl iodide, iodine can also be brought into contact with the adsorber according to the abovementioned embodiments and adsorbed by the latter. The methyl iodide and/or the iodine can be radioactive, in particular if the method is used in nuclear power plants, reprocessing plants or fuel element storage facilities.

The adsorber of embodiment examples can be produced by methods in which the iodide-adsorbing metal is introduced into a hydrophobic zeolite material. As already explained, an intrinsically hydrophobic zeolite, as described above, can be used as zeolite material. The adsorber is preferably produced by metal loading, e.g. impregnation, of a finished shaped body made from or coated with the zeolite material.

Another example of a method for producing the adsorber comprises: a) incorporating a compound of the iodide-adsorbing metal, hereafter also called metal compound, into the zeolite material; b) wet milling the zeolite material loaded with metal compound with a support material which can be porous; c) drying the mixture comprising the loaded zeolite material and the support material. After step a) and before step b) a fixing step can be carried out, in which the metal compound is fixed to the zeolite material. Furthermore, a stabilizing step can take place to stabilize the adsorber. A silica sol such as Bindzil, which is liquid and is porous after drying, is frequently used as support material. In this way it is possible to obtain an adsorber comprising a porous support material as well as a zeolite material, the inner surface of which is loaded with the iodide-adsorbing metal.

For example the wet mixture obtained in step b) or the dried mixture obtained in step c) can be applied to a support in a slurry or in a washcoat. Within the context of this invention, by adsorbers can thus also be meant adsorbers produced by coating a support body with a typically porous layer containing the at least one iodide-adsorbing metal.

The introduction of the compound of the iodide-adsorbing metal here also referred to as metal compound, into the zeolite material or into the zeolite can be carried out in order to produce embodiments of the invention by means of solid substance exchange or solid body ion exchange. For example the introduction takes place by means of mixing the zeolite material with the metal compound in the dry state in a ball mill and with subsequent tempering at higher temperatures, preferably at a temperature of from 450 to 650° C. Alternatively the metal compound is introduced by impregnating the zeolite material with a solution of the metal compound, for example by spraying the solution onto the zeolite material. The impregnation can also be carried out in a chamber in which a turbulent flow brought about by an application of suction to the chamber and a below-atmospheric pressure prevail. According to another method for producing an embodiment, the metal compound is introduced by impregnating the zeolite material with a solution of the metal compound by means of the pore filling method. In this, the zeolite material is brought into contact with a quantity of solution, the volume of which corresponds to the pore volume of the zeolite material used.

In a further example, firstly an e.g. honeycomb-shaped support is coated with a washcoat containing the zeolite material and a porous support material, e.g. porous silica. The coated support is then calcined. Subsequently the coated support is impregnated for example with a nitrate solution of the iodide-adsorbing metal. The impregnated coated support is then dried.

In the adsorber production method, the corresponding nitrates, acetates, oxalates, tartrates, formates, amines, sulphites, carbonates, halides or hydroxides can be used as compounds of the iodide-adsorbing metal or of the promoter.

In the production of the adsorber according to embodiments the zeolite material can, furthermore, be a microporous or a mesoporous zeolite material, for example of the BEA-type structure or of the MCM family.

The adsorber of embodiments can moreover be an adsorber with polymodal pore distribution, i.e. it contains micropores and mesopores as well as macropores. In the context of the present invention, by the terms micropores, mesopores and macropores are meant pores which have a diameter of <1 nanometer (micropores), a diameter of from 1 to 50 nanometers (mesopores), and a diameter of >50 nanometers (macropores) respectively. The proportion of the micro and meso/macropores is determined by the so-called "t-plot" method according to ASTM D-4365-85.

The adsorber according to embodiments can for example comprise a microporous zeolite material, which contains at least one iodide-adsorbing metal, and a porous $SiO_2$-containing binder, wherein the adsorber can have a proportion of micropores, e.g. with a diameter <1 nm, of more than 70% relative to the total pore volume of the adsorber. Furthermore, the zeolite material can have an aluminium proportion of less than 2 mol. %. The zeolite material/binder weight ratio (relative to the respective dry masses) can be 99:1 to 1:99. A pure $SiO_2$ binder which contains few meso- and macropores, e.g. Bindzil 2034 DI suspension (Eka Chemicals AB, Bohus/Sweden) can be used as $SiO_2$-containing binder. It has been found that adsorbers which comprise a microporous zeolite material containing an iodide-adsorbing metal, and a pure $SiO_2$ binder having few meso- and macropores, have a clearly higher iodide adsorption capacity.

Such an adsorber of embodiments can be produced by a) introducing a compound of the iodide-adsorbing metal into a microporous zeolite material; b) Mixing the thus-produced zeolite material loaded with metal compound with a porous $SiO_2$-containing binder and a solvent; and c) Drying the mixture comprising the zeolite material loaded with the metal compound and the binder. The mixture obtained in step b) can be applied to a support, also referred to as support body.

In a further method for producing the adsorber of embodiments an adsorber is produced which, in addition to the iodide-adsorbing metal, contains a metal-containing promoter, here also referred to as a bimetallic adsorber. This example is described with reference to the production of an Ag and Pb-containing adsorber, which can be obtained by: impregnating a support material made from a hydrophobic zeolite with sulphur-free Ag and Pb compounds, and air-drying the impregnated zeolite support material. Solutions of the nitrates, for example, can be used as Ag and Pb compounds. The drying of the impregnated zeolite support material can preferably be carried out below the decomposition point of the Ag and Pb compounds. This method can, furthermore, include the following steps: producing a washcoat from the impregnated zeolite support material, coating a support body with the washcoat, and air-drying the coated support body.

In this way an adsorber according to embodiments can be produced, wherein the adsorber contains a bimetallic composition containing Ag and Pb on a zeolite support material. The bimetallic composition can have a BET surface area of more than 400 m²/g. In particular the bimetallic composition can have an Ag content of from 1 to 50 wt. % relative to the composition and/or a Pb content of from 1 to 30 wt. % relative to the composition. The composition can furthermore be applied to a support body as a washcoat coating, wherein the adsorber has 0.5 to 12 wt. % Ag and/or 1 to 6 wt. % Pb relative to the coated washcoat. In particular the bimetallic composition or the washcoat coating can have an Ag/Pb weight ratio of from 6:1 to 1:1. In the adsorber of this example, furthermore, Ag and Pb can be substantially located in the pores of the zeolite support material and be present in aggregates of <5 nm.

Measurement Methods

Elemental Analysis with ICP:

ICP-AES (Inductively coupled plasma atomic emission spectroscopy) was carried out with an ICP Spectro Modula/Arcos device in order to ascertain the elemental composition, or the $SiO_2/Al_2O_3$ ratio. The following chemicals were used: sulphuric acid 98% p.a., hydrofluoric acid 37% p.a., hydrochloric acid 37% p.a. The sample was finely ground.

For Si and Al, a 100 mg sample was weighed in a 100 ml plastic beaker, and 1 ml of sulphuric acid and 4 ml of hydrofluoric acid were added. Solubilization was carried out in a water bath for 5 minutes at 85° C. until a clear solution was produced. Tempering, filling and shaking were then carried out. All the elements were measured using the ICP, as well as corresponding standards. Si was measured with the following settings: wavelength: 288, 158 nm. Al was measured with the following settings: wavelength: 396, 152 nm.

For Ag and/or Pb the quantity of sample weighed in was such that it contained approximately 3 mg Ag or Pb respectively. Then 6 ml of each of hydrofluoric acid and hydrochloric acid were added. Heating to 180° C. over 30 minutes was then carried out, accompanied by stirring, to produce a clear solution. Tempering, filling and shaking were then carried out. All the elements were measured using the ICP, as well as corresponding standards. Ag was measured with the following settings: wavelength: 214, 423 nm. For Pb the wavelength was: 168 nm.

All the standards were adjusted with HF and HCl or $H_2SO_4$. The evaluation followed the following calculation: w(E*in percent)=β(E*measurement value in mg/l)×V(measuring flask in 1)×100/m(initial weight in mg) (E*=respective element).

BET Surface Area:

This is determined according to the BET method in accordance with DIN 66131; a publication of the BET method is also found in J. Am. Chem. Soc. 60,309 (1938). The sample to be determined was dried in a U-shaped quartz reactor at 200° C. under Ar atmosphere (F=50 ml(min) for 1.5 h). The reactor was then cooled to room temperature, evacuated and dipped into a Dewar flask with liquid nitrogen. The nitrogen adsorption was carried out at 77 K with an RXM 100 sorption system (Advanced Scientific Design, Inc.).

Pore Volume and Pore Size:

The integral pore volume was determined in accordance with DIN 66134, determination of the pore-size distribution and of the specific surface area of mesoporous solids by nitrogen sorption according to BJH (process according to Barrett, Joyner and Halenda). The proportion of the micro and meso/macropores is determined by means of the so-called t-plot method according to ASTM D-4365-85.

Embodiment Examples and Comparison Examples

A commercially available BEA zeolite from Süd-Chemie AG (H-BEA-150), which is highly hydrophobic due to its high $SiO_2/Al_2O_3$ modulus of 150, was shaped into spheres with a diameter of 3 mm. $SiO_2$ in a quantity of 10 wt. % was used as binder.

The thus-obtained shaped body was impregnated with silver nitrate according to the incipient wetness method and set to an elemental silver content of 12 wt. % (Adsorber A).

Adsorber A was additionally doped with different quantities of lead nitrate according to the incipient wetness method (1 wt. % Pb=Adsorber B; 3 wt. % Pb=Adsorber C; 6 wt. % Pb=Adsorber D; 12 wt. % Pb=Adsorber E).

Comparison examples were 13× zeolites (Manufacturer Süd-Chemie AG) with a modulus of 1.5, which were formed as spheres of the same size as the embodiment examples and were doped with 12 wt. % silver (Adsorber F) and with 12% silver and 12% lead (Adsorber G) using the respective nitrates according to the incipient wetness method.

In addition a conventional adsorber in the form of aluminium oxide spheres of the same size as the embodiment examples with 12 wt. % Ag and silanized with propyl triethoxysilane (Dynasylan® PTEO from EVONIK) was tested as a further comparison example (Adsorber H).

The methyl iodide retention and the hydrogen formation/release in the flow-through adsorber bed of the embodiment examples and comparison examples were measured.

The retention of the methyl iodide was measured in a heatable throughflow apparatus. The throughflow was set to 100 l/h. As test gas, 200 ppmv methyl iodide was added to the respective air-water vapour mixture specified in Table 1. For each measurement, 5 g of the material to be examined was incorporated into the apparatus. The initial and final methyl iodide concentrations were measured by means of FID. The ratio of final concentration to initial concentration after a through-flow period of 5 minutes serves as retention value.

The hydrogen formation/release was again measured in a throughflow apparatus. Here, the apparatus was subjected to a throughflow of 100 l/h water vapour-saturated air (3.2 Vol. % $H_2O$) at room temperature. The apparatus consists of two segments each with a thermocouple at the inlet and outlet. The first segment contained 5.0 g of the respective sample to be examined. The second segment contained an oxidation catalyst doped with platinum, which re-oxidizes the hydrogen formed to form water. The reaction heat thereby released, which can be measured as temperature difference between inlet and outlet in the second segment, serves as a measure for the quantity of hydrogen formed, as there are no further components that can be oxidized at room temperature present in the test gas.

1 K temperature increase corresponds approximately to the formation of 0.014 Vol. % $H_2$.

The measured methyl iodide retention values and the quantity of hydrogen formed were then compared with those of the comparison examples, as can be seen from the following Tables 1 and 2.

TABLE 1

| | | CH₃I retention | | | |
|---|---|---|---|---|---|
| Adsorber | According to the invention | At RT and AH of 70% | At RT and 50% H₂O vapour | At RT and 90% H₂O vapour | At 200° C. and 90% H₂O vapour |
| A | yes | >99% | >99% | >99% | >99% |
| B | yes | >99% | >99% | >99% | >99% |
| C | yes | >99% | >99% | >99% | >99% |
| D | yes | >99% | >99% | >99% | >99% |
| E | yes | >99% | >99% | >99% | >99% |
| F | no | 85% | ca. 80% | ca. 70% | ca. 60% |
| G | no | 85% | ca. 80% | ca. 70% | ca. 60% |
| H | no | 98% | ca. 90% | ca. 85% | ca. 30% |

TABLE 2

| | | Hydrogen release | |
|---|---|---|---|
| | According to the invention | Temperature difference in reactor segment 2 in K | Stability of hydrophobicity |
| A | yes | traces | 3 | up to >1000° C. |
| B | yes | traces | 3 | up to >1000° C. |
| C | yes | not measurable | <1 | up to >1000° C. |
| D | yes | not measurable | <1 | up to >1000° C. |
| E | yes | not measurable | <1 | up to >1000° C. |
| F | no | traces | 2 | no hydrophobicity |
| G | no | not measurable | <1 | no hydrophobicity |
| H | no | not measurable | <1 | up to 180° C. |

RT = Room temperature = 25° C.
AH = Air humidity

From Table 1 it can be seen that the embodiment examples at different temperatures and air humidities or water vapour concentrations in the atmosphere exhibited a $CH_3I$ retention of more than 99%, while those of the comparison examples led to less than 99% CH₃I retention. The iodide adsorption capacity of the embodiment examples is thus clearly better than that of the comparison examples.

Table 2 further shows that all the embodiment examples and comparison examples brought about only a low, or non-measurable hydrogen release.

The silver-containing BEA-150 zeolites used in the embodiment examples and the corresponding adsorbers are in addition characterized by a high temperature resistance of the hydrophobicity up to more than 1000° C. This is true in particular in comparison with comparison example H, which is provided with hydrophobic properties by silanization, the silane layer of which is, however, already thermally decomposable at 180° C.

The invention claimed is:

1. An iodide or iodine adsorber, comprising a zeolite containing at least one iodide- or iodine-adsorbing metal or a compound thereof, wherein the zeolite is a hydrophobic zeolite having an $SiO_2/Al_2O_3$ ratio>30, and wherein the zeolite is BEA.

2. The adsorber according to claim 1, in which the zeolite is an intrinsically hydrophobic zeolite.

3. The adsorber according to claim 1, in which the zeolite is microporous.

4. The adsorber according to claim 1, in which the zeolite or the adsorber has a proportion of micropores of more than 70%, relative to the total pore volume of the zeolite or of the adsorber.

5. The adsorber according to claim 1, in which the zeolite is an aluminium silicate.

6. The adsorber according to claim 1, in which at least one promoter is contained for reducing the water decomposition by the iodide-adsorbing metal.

7. The adsorber according to claim 6, in which the promoter comprises lead.

8. The adsorber according to claim 1, in which the zeolite or the adsorber has a BET surface area of 10 to 1000 m²/g.

9. The adsorber according to claim 1, in which the adsorber is formed as bulk material.

10. The adsorber according to claim 9, in which the adsorber is formed as extrudate, as shaped bodies or as particles coated with the zeolite.

11. A method for the adsorption of gaseous methyl iodide, gaseous radioactive methyl iodide, gaseous iodine and/or gaseous radioactive iodine, comprising contacting gaseous methyl iodide, gaseous radioactive methyl iodide, gaseous iodine and/or gaseous radioactive iodine with the adsorber of claim 1.

12. The method according to claim 11, in which the adsorber is used in or in the vicinity of nuclear power plants, reprocessing plants or fuel element storage facilities; and/or in which the adsorber is used together with a hydrogen recombination catalyst.

13. A process for the adsorption of gaseous methyl iodide, in which gaseous methyl iodide is brought into contact with an adsorber according to claim 1.

14. A process according to claim 13, in which the gaseous methyl iodide is radioactive; and/or in which gaseous iodine and/or gaseous radioactive iodine is additionally adsorbed by the adsorber.

15. The adsorber according to claim 1, wherein the iodide or iodine is adsorbed from a gas phase onto said zeolite.

16. The adsorber according to claim 1, wherein the zeolite has an $SiO_2/Al_2O_3$ ratio>50.

17. The adsorber according to claim 1, wherein the iodide- or iodine-adsorbing metal is selected from silver, yttrium, cerium, magnesium, sodium, tin, and lead.

18. The adsorber according to claim 1, wherein the iodide-adsorbing metal is situated in the pores of the zeolite.

19. The adsorber according to claim 1, wherein the zeolite has an $SiO_2/Al_2O_3$ ratio>100.

20. The adsorber according to claim 6, wherein the content of iodide- or iodine-adsorbing metal in the zeolite or in the adsorber is 0.1 to 50 wt. %.

21. The adsorber according to claim 6, wherein the content of promoter in the zeolite or in the adsorber is 1 to 30 wt. %.

22. The adsorber according to claim 1, wherein the integral pore volume of the zeolite or of the adsorber is greater than 100 mm³/g.

23. The adsorber according to claim 1, wherein the adsorber comprises a support comprising the zeolite.

24. The adsorber according to claim 1 wherein the adsorber comprises a support wherein the support comprises a washcoat comprising the zeolite.

25. The adsorber according to claim 9, wherein the adsorber is formed as extrudate, as shaped bodies, or as particles coated with the zeolite.

26. The adsorber according to claim 24, wherein the adsorber is formed as extrudate, as shaped bodies or as particles coated with the zeolite.

27. The adsorber according to claim 9 wherein the adsorber is formed honey-combed-shaped or plate-shaped.

28. The adsorber according to claim 24 wherein the adsorber is formed honey-combed-shaped or plate-shaped.

29. The adsorber according to claim 9 wherein the support is formed honey-combed-shaped or plate-shaped.

30. The adsorber according to claim 24 wherein the support is formed honey-combed-shaped or plate-shaped.

31. An iodide or iodine adsorber, comprising a BEA zeolite comprising between 10% and 20% of at least one metal or compound thereof capable of methyl-iodide adsorption, wherein the metal or compound thereof is selected from the group consisting of silver, yttrium, cerium, magnesium, sodium, tin and lead; and wherein the BEA zeolite has a ratio of $SiO_2/Al_2O_3$ between 100 and 250, and is microporous.

32. The iodide or iodine adsorber according to claim 31, wherein the metal or compound thereof is silver.

33. The iodide or iodine adsorber according to claim 31, further comprising at least one promoter for reducing the water decomposition by the iodide-adsorbing metal, wherein the promotor comprises lead.

34. The iodide or iodine adsorber according to claim 31, wherein a ratio of the at least one metal or compound thereof capable of methyl-iodide adsorption to the lead is from 6:1 to 1:1.

* * * * *